United States Patent
Sano et al.

(10) Patent No.: US 6,749,818 B2
(45) Date of Patent: *Jun. 15, 2004

(54) SOLUTION PREPARING APPARATUS

(75) Inventors: Yoshihiko Sano, Osaka (JP); Hidetoshi Saio, Osaka (JP)

(73) Assignee: Nipro Corporation, Osaka (JP)

( * ) Notice: Subject to any disclaimer, the term of this patent is extended or adjusted under 35 U.S.C. 154(b) by 312 days.

This patent is subject to a terminal disclaimer.

(21) Appl. No.: 09/912,317

(22) Filed: Jul. 26, 2001

(65) Prior Publication Data

US 2002/0012619 A1 Jan. 31, 2002

(30) Foreign Application Priority Data

Jul. 26, 2000 (JP) ....................................... 2000-224892

(51) Int. Cl.$^7$ ................ B01D 11/04; B01D 1/00; B01D 35/00; B01D 11/00; B01F 15/02
(52) U.S. Cl. ................ 422/255; 422/256; 422/261; 422/281; 422/285; 422/292; 210/85; 210/198.1; 210/252; 210/321.71; 210/335; 210/416.1; 210/646; 137/896; 366/132; 366/136
(58) Field of Search ................. 422/185, 119, 422/255, 261, 263, 267, 269, 272, 281–282, 284–285, 292, 294–295, 300, 307, 311, 902; 366/132, 136; 210/96.1, 195.1, 257.1, 321.71, 335, 646, 416.1, 136, 132

(56) References Cited

U.S. PATENT DOCUMENTS

| | | | |
|---|---|---|---|
| 3,653,640 A | * | 4/1972 | deHass |
| 4,293,409 A | * | 10/1981 | Riede et al. |
| 4,606,826 A | * | 8/1986 | Sano et al. |
| 4,814,073 A | * | 3/1989 | Shouldice |
| 4,935,125 A | * | 6/1990 | Era et al. |
| 6,277,272 B1 | * | 8/2001 | Nikaido et al. |

* cited by examiner

Primary Examiner—Robert J. Warden, Sr.
Assistant Examiner—Monzer R. Chorbaji
(74) Attorney, Agent, or Firm—Kubovcik & Kubovcik

(57) ABSTRACT

A cost effective solution preparing apparatus includes a chamber which is divided into two compartments by a movable partition; a dissolving solution supply line for supplying a dissolving solution to the first compartment of the chamber; a solution tank connected with the first compartment and the second compartment through a first solution preparing line and through a second solution preparing line, respectively; a transporting pump provided in the second solution preparing line; a concentration meter; a solution transporting line for transporting the solution prepared and filled in the second compartment to a point of use; and a circulating line, in which the solution tank is exemplified as a U-shape tank constructed of a relatively small-diameter upstream tank portion and a relatively large-diameter downstream tank portion, and at least one filter is provided in a downstream portion of the downstream tank portion.

7 Claims, 2 Drawing Sheets

SOLUTION PREPARING APPARATUS

TECHNICAL FIELD OF THE INVENTION

The present invention relates to a solution preparing apparatus for dissolving powder (including granulated powder) in a dissolving solution. The solution preparing apparatus of the present invention is particularly suitable for preparing a dialysate.

BACKGROUND OF THE INVENTION

Hitherto, preparation of solutions has been carried out in a tank system. In the tank system, prescribed quantities of a dissolving solution and powder are introduced into a solution tank and stirred by a stirring pump or a stirring blade and mixed to form a solution. The prepared solution is transported to a point of use by a delivery pump. At this time, the level of the surface of the solution in the solution tank is lowered, and a negative pressure is generated in the solution tank and thus outside air is introduced into the solution tank. The introduction of air occurs in the tank system because the solution tank is generally opened to the air to prevent breakage of the solution tank itself by a negative pressure generated therein. Therefore, in many cases, an air filter is provided at a portion opened to the air to prevent bacteria or the like contained in the outside air from entering. The use of an air filter results in problems and a high cost for replacing the air filter on a regular basis. As a matter of fact, there are cases where a filter that prevents only dust is used, or even no filter is used considering problems and cost. In addition, in a tank system, when an attempt is made to prepare a large quantity of solution at a time, a large solution tank is necessary, thereby disadvantageously increasing the size of the apparatus itself. Moreover, since many stirring pumps and delivery pumps are necessary, the operating noise may disadvantageously be too loud.

With a view to the circumstances described above, an object of the present invention is to provide a cost effective solution preparing apparatus in which replacement of an air filter for preventing bacteria or the like from entering into the solution tank is essentially unnecessary, and miniaturization of the entire system and lowering of operation noise are possible.

SUMMARY OF THE INVENTION

After dedicated studies, the inventor found that the above-described object can be achieved by utilizing a chamber which is divided by a movable partition into two compartments so that a solution can be prepared within a circuit containing these two compartments while substantially preventing outside air from entering therein, and reached the present invention. More specifically, the present invention relates to a solution preparing apparatus comprising a chamber which is divided into two compartments by a movable partition; a dissolving solution supply line for supplying a dissolving solution to the first compartment of the chamber; a solution tank connecting the first compartment to the second compartment through a first solution preparing line connected to the first compartment and the solution tank, and through a second solution preparing line connected to the solution tank and the second compartment; a transporting pump provided in the second solution preparing line; a concentration meter; a solution transporting line for transporting solution filled in the second compartment to the point of use; and a circulating line connecting the first solution preparing line between the first compartment and the solution tank to the second solution preparing line between the transporting pump and the second compartment; wherein the solution tank is provided with an upstream tank portion and a downstream tank portion in liquid communication at the bottoms thereof, and at least one filter provided in a downstream portion of the downstream tank portion.

The solution flows from the first compartment to the solution tank through the first solution preparing line, and from the solution tank to the second compartment through the second solution preparing line. The solution tank comprises an upstream tank portion connected to the first compartment through the first solution preparing line and a downstream tank portion connected to the second compartment through the second solution preparing line. Further, the solution tank has an inlet for the powder.

The solution tank may be any shape as long as it is provided with an upstream tank portion and a downstream tank portion in liquid communication at the bottoms thereof. For instance, the tank includes a U-shape tank or a tubular tank where the tubular tank is divided into an upstream tank portion and a downstream tank portion by a vertically arranged diaphragm. An U-shape tank constructed of a relatively small-diameter upstream tank portion and a relatively large-diameter downstream tank portion connected by a small-diameter bottom portion so as to communicate with each other, or a tubular tank divided into an upstream tank portion and a downstream tank portion and which has a large diameter portion at a location downstream thereof by a vertically arranged diaphragm is also preferable. The upstream tank portion of the solution tank may be provided with a level detecting sensor, and preferably, the downstream tank portion of the solution tank is provided with a powder level sensor in order to ensure a sufficient supply of powder. In addition, it is preferable to provide a heater at a location downstream of the solution tank for keeping the solution at a constant temperature.

The circulating line connects the first solution preparing line between the first compartment and the solution tank with the second solution preparing line between the transporting pump and the second compartment.

DETAILED DESCRIPTION OF THE INVENTION

Figure 1:
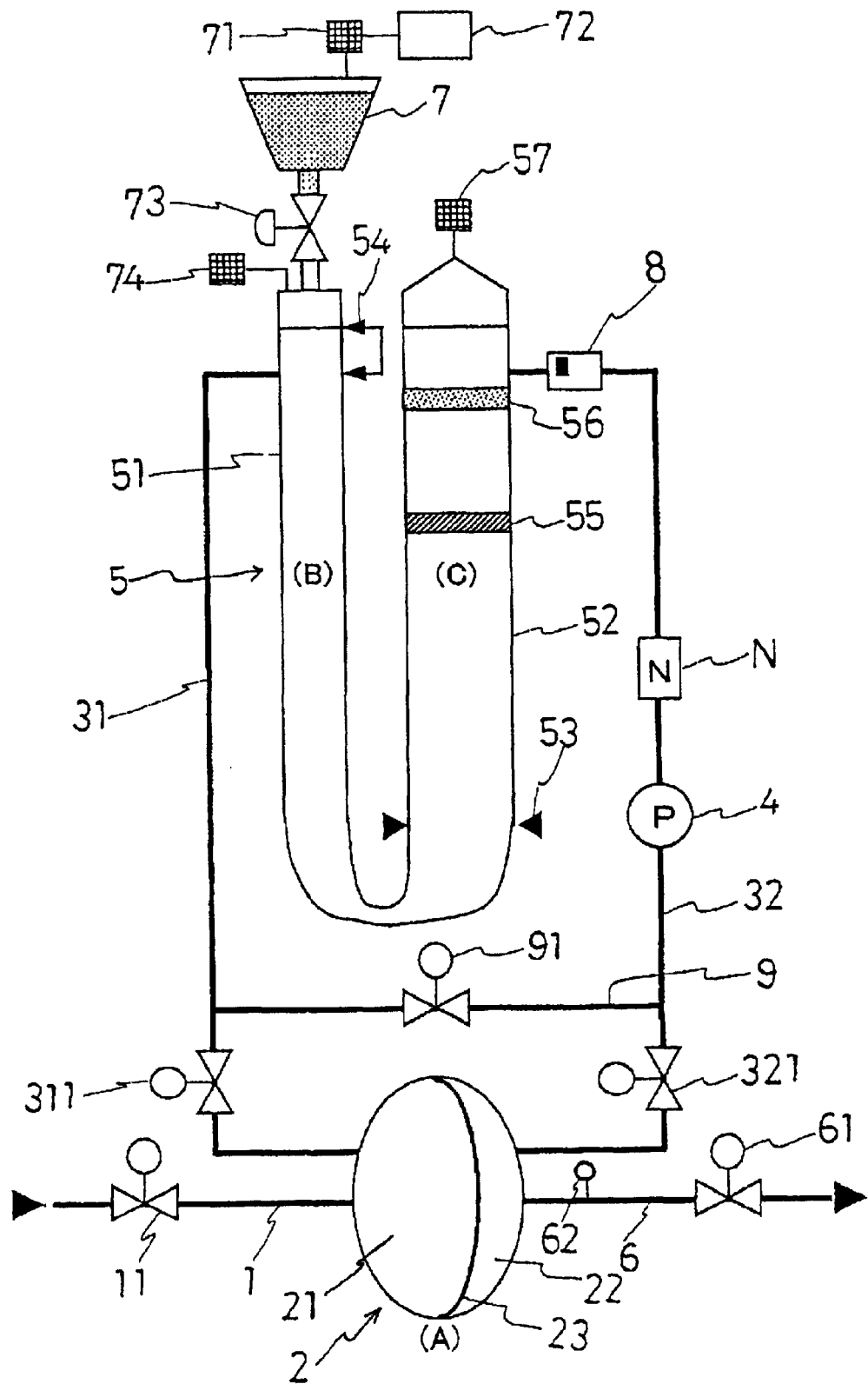
FIG. 1 is a circuit diagram showing an embodiment of the present invention

Referring now to the drawings, embodiments of the present invention will be described.

As shown in FIG. 1, a solution preparing apparatus of the prevent invention comprises a chamber 2 the inside of which is divided into two compartments 21, 22 by a movable partition 23; a dissolving solution supply line 1 for supplying a dissolving solution to the first compartment 21 of the chamber 2; a solution tank 5; first and second solution preparing lines 31, 32 connecting the solution tank 5 with the first compartment 21 and with the second compartment 22, respectively; a concentration meter N; a transporting pump 4 provided in the second solution preparing line 32; a solution transporting line 6 for transporting the solution prepared and filled in the second compartment 22 to the point of use; powder supply means 7; and a circulating line 9.

The solution tank 5 is a U-shape tank constructed of a relatively small-diameter upstream tank portion 51 and a relatively large-diameter downstream tank portion 52. Filters 55, 56 are provided in a downstream portion of the downstream tank portion 52.

Switch valves 11, 311, 321, 61 and 91 are provided in the dissolving solution supply line 1, solution preparing lines 31, 32, solution transporting line 6, and circulating line 9, respectively.

A circulating line 9 connects the first solution preparing line 31 between the first compartment 21 and the solution tank 5 to the second solution preparing line 32 between the transporting pump 4 and the second compartment 22. In other words, the circulating line 9 is a line for connecting the first solution preparing line 31 with the second solution preparing line 32 at locations downstream from the switch valve 311 and upstream from the switch valve 321, so that the solution can circulate in a circuit comprising the first solution preparing line 31, the solution tank 5, the second solution preparing line 32, and the circulating line 9 by the transporting pump 4. Reference numerals 57, 71, 74 designate air filters, and reference numeral 73 designates a switch valve for powder supply.

Figure 2:
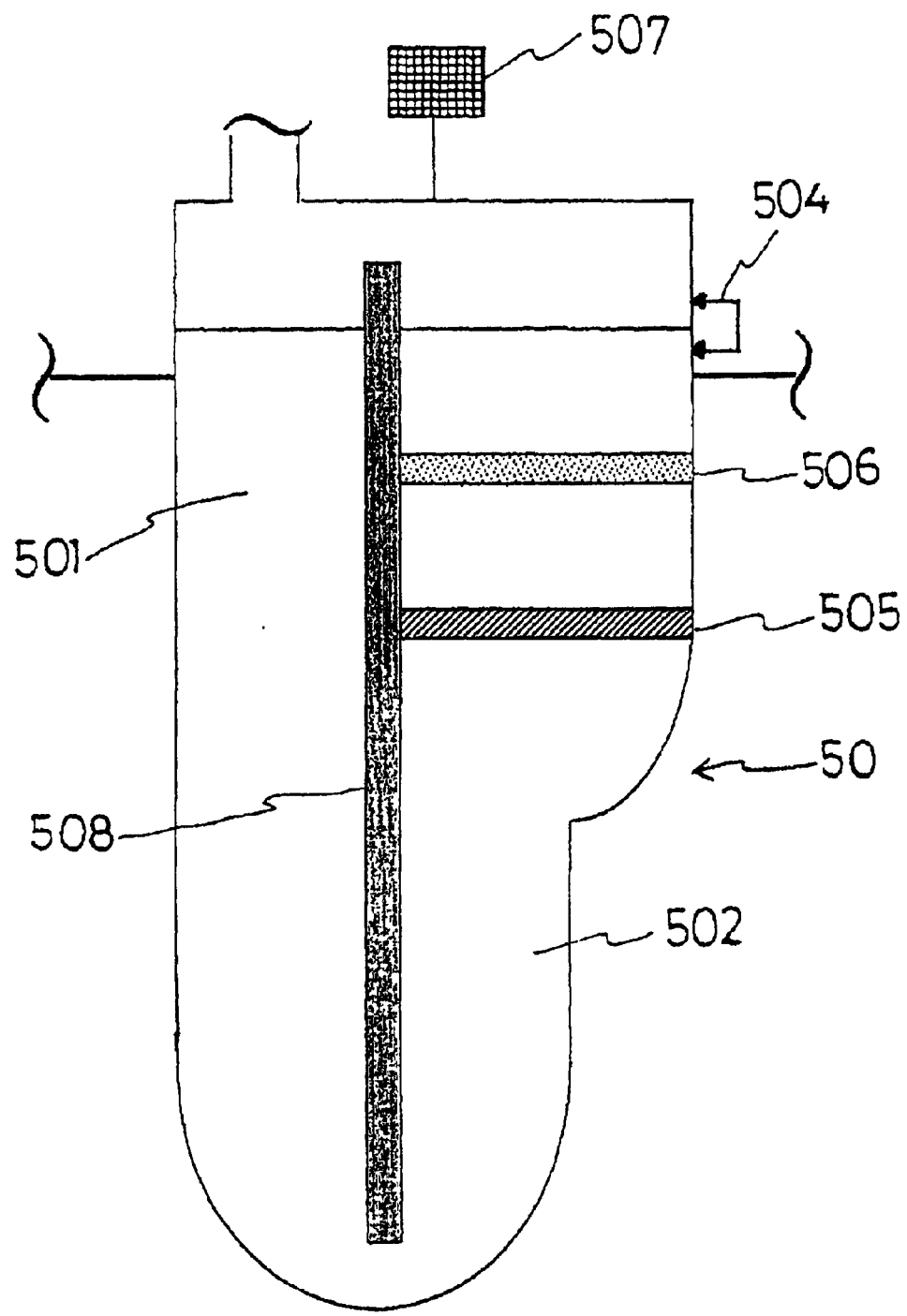
FIG. 2 is a schematic diagram showing another embodiment of the solution tank illustrated in FIG. 1.

The solution tank 5 is a U-shape tank constructed of a relatively small-diameter upstream tank portion 51 and a relatively large-diameter downstream tank portion 52 connected in communication with each other by a narrow constricted bottom portion. The upstream tank portion 51 is preferably provided with a level detecting sensor 54, and filters (preferably two types of the filters; a coarse-grained filter 55 and a fine-grained filter 56) for removing undissolved particles from the mixture of powder and dissolving solution are provided in a downstream portion of the downstream tank portion 52. It is also possible to provide a powder level sensor 53 upstream of the tank portion 52 for preventing the powder from not being sufficiently supplied to the solution tank 5. As shown in FIG. 2, the solution tank may be a tubular tank 50 divided by a vertically arranged diaphragm 508. In the figure, reference numeral 501 designates an upstream tank portion, reference numeral 502 designates a downstream tank portion, reference numeral 504 designates a level detecting sensor, reference numerals 505, 506 designate filters, and reference numeral 507 designates an air filter. Though a powder level sensor is not shown in the figure, a level sensor may be mounted parallel to the diaphragm 508. The cross sectional area of the filters 505 and 506 is preferably larger than the cross sectional area of the downstream tank portion because the flow rate through the filters can be comparatively reduced.

An air filter 74 and a switch valve for powder supply 73 are provided between the upstream tank portion 51 and the powder supply means 7 mounted above the upstream tank portion. The powder supply means 7 is provided with an air filter 71 for preventing contamination by incoming outside air, and a dehumidifier 72 for preventing humidity. In addition, an air filter 57 is mounted at the upper portion of the downstream tank portion 52, and normally, a heater 8 is provided in the second solution preparing line 32 upstream of the transporting pump 4 for heating the mixture and preventing the solution ingredients from depositing. The concentration meter N may be mounted at any position in the circuit comprising the first solution preparing line 31, the solution tank 5, the second solution preparing line 32, and the circulating line 9.

In the operation to prepare a solution, the switch valves 11, 61 are opened but the switch valves 91, 311, 321 are initially closed and a dissolving solution is supplied from the dissolving solution source (not shown) through the dissolving solution supply line 1 to the first compartment 21 of the chamber 2. Then, the air contained in the second compartment 22 is exhausted through the solution transporting line 6 and, thus, the movable partition 23 moves toward the second compartment 22. The movement of the movable partition 23 continues until the capacity of the second compartment 22 becomes zero. That is, it continues until the dissolving solution of the same quantity as the capacity of the chamber 2 is filled into the first compartment 21. (step 1)

The internal pressure in the solution transporting line 6 suddenly drops when the capacity of the second compartment 22 becomes zero. A pressure gauge 62 is provided in the solution transporting line 6 between the second compartment 22 and the switch valve 61. When the decrease of the internal pressure in the solution transporting line 6 is detected by the pressure gauge 62, the switch valve 311 is opened, and the switch valve 61 is closed, so that the dissolving solution supplied from the dissolving solution source through the dissolving solution supply line 1 to the first compartment 21 is supplied to the solution tank 5 through the first solution preparing line 31. (step 2)

When the level of the dissolving solution supplied to the solution tank 5 reaches a prescribed level (this can be determined arbitrarily) in the upstream tank portion 51, the level detecting sensor 54 is activated and the switch valves 11, 311 are closed, the switch valve 91 is opened, and the transporting pump 4 is activated, and simultaneously, powder is supplied to the upstream tank portion 51 of the solution tank 5. Then, the solution (a mixture of powder and dissolving solution) is circulated in the circuit comprising the first solution preparing line 31, the solution tank 5, the second solution preparing line 32, and the circulating line 9. The powder is supplied to the upstream tank portion 51 of the solution tank 5 continuously after the transporting pump 4 is started, and is controlled by the switch valve 73 so that the position of powder in the downstream tank portion 52 is higher than the position of the powder level sensor 53. (step 3)

When the concentration of the solution reaches a prescribed value (which is set to a concentration close to saturation and the concentration of the solution measured by the concentration meter N at this time remains substantially constant), the switch valve 91 is closed, and switch valves 311 and 321 are opened. Then, the solution is supplied through the second solution preparing line 32 to the second compartment 22 and, at the same time, the dissolving solution in the first compartment 21 of the same quantity as the solution supplied to the second compartment 22 is supplied through the first solution preparing line 31 to the solution tank 5. At this time, the movable partition 23 moves toward the first compartment 21. The movement of the movable partition 23 continues until the capacity of the first compartment 21 becomes zero, that is, it continues until the same quantity of solution as the capacity of the chamber 2 is filled into the second compartment 22. During the solution preparing process, outside air hardly enters into the solution tank 5 because the level of liquid in the solution tank 5 is kept constant. (step 4)

An increase in the inner pressure of the second compartment 22 is detected by the pressure gauge 62 (that is, the increase in the inner pressure of the second compartment 22 that occurs when the capacity of the first compartment 21 becomes zero) and then, the transporting pump 4 is stopped, the switch valves 311 and 321 are closed, and the switch valves 11, 61 are opened. As a result, the dissolving solution is supplied from the dissolving solution source through the dissolving solution supply line 1 to the first compartment 21 of the chamber 2. At this time, the movable partition 23 moves toward the second compartment 22, and the solution in the second compartment 22 is transported through the solution transporting line 6 to the point of use. The movement of the movable partition 23 and the transportation of the solution in the second compartment 22 to the point of use continue until the capacity of the second compartment 22 becomes zero, that is, the movement and the transportation continue until the same quantity of the dissolving solution as the capacity of the chamber 2 is filled into the first compartment 21. (step 5)

Hereafter, the same procedures (step 3, 4 and 5) are repeated to prepare the desired solution such as dialysate. The procedures of step 3 and step 5 can take place simultaneously.

As is clear from the description above, the liquid transporting equipment of the present invention is advantageous in terms of cost because replacement of the filter and stirring pump provided outside the apparatus are not necessary, and the number of the delivering pumps can be reduced. Since a large solution tank is not necessary, miniaturization of the system itself is possible. Further, as there is only one delivering pump used, the operating noise can significantly be reduced.

What is claimed is:

1. A solution preparing apparatus comprising:
   a chamber, an inside of which is divided into a first compartment and a second compartment by a movable partition;
   a dissolving solution supply line for supplying a dissolving solution to the first compartment of the chamber;
   a solution tank connected with the first compartment through a first solution preparing line and connected with the second compartment through a second solution preparing line;
   a transporting pump provided in the second solution preparing line
   a concentration meter;
   a solution transporting line for transporting solution filled in the second compartment to the point of use; and
   a circulating line connecting the first solution preparing line between the first compartment and the solution tank to the second solution preparing line between the transporting pump and the second compartment;
   said solution tank being provided with an upstream tank portion and a downstream tank portion in liquid communication at bottoms thereof, and at least one filter provided in a downstream portion of the downstream tank portion.

2. The solution preparing apparatus claimed in claim 1, wherein the solution tank is a U-shaped tank constructed of a relatively small-diameter upstream tank portion and a relatively large-diameter downstream tank portion connected at bottoms thereof by a bottom portion of the U-shaped tank having small-diameter so as to communicate with each other.

3. The solution preparing apparatus claimed in claim 1, wherein the solution tank is a tubular tank divided into an upstream tank portion and a downstream tank portion by a vertically arranged diaphragm.

4. The solution preparing apparatus claimed in claim 1, wherein a powder supply means is provided above the upstream tank portion of the solution tank.

5. The solution preparing apparatus claimed in claim 1, wherein a level detecting sensor is provided in the upstream tank portion of the solution tank.

6. The solution preparing apparatus claimed in claim 1, wherein a powder level sensor is provided in the downstream tank portion of the solution tank.

7. The solution preparing apparatus claimed in claim 1, wherein a heater is provided in the second solution preparing line downstream of the solution tank.

* * * * *